United States Patent
McIntosh

(10) Patent No.: US 8,776,801 B2
(45) Date of Patent: Jul. 15, 2014

(54) QUASI-TRIANGULAR IN-EAR DEVICE

(75) Inventor: Ian McIntosh, Alexandria (CA)

(73) Assignee: Sonomax Technologies Inc., Montréal (QC) (CA)

( * ) Notice: Subject to any disclaimer, the term of this patent is extended or adjusted under 35 U.S.C. 154(b) by 350 days.

(21) Appl. No.: 12/929,053

(22) Filed: Dec. 27, 2010

(65) Prior Publication Data

US 2011/0155147 A1 Jun. 30, 2011

Related U.S. Application Data

(60) Provisional application No. 61/282,175, filed on Dec. 24, 2009.

(51) Int. Cl.
*A61F 11/06* (2006.01)
*A61F 11/08* (2006.01)

(52) U.S. Cl.
USPC .......................... 128/864; 181/130; 181/135

(58) Field of Classification Search
USPC ................. 128/864, 866; 181/129–130, 135; 381/328, 380
See application file for complete search history.

(56) References Cited

U.S. PATENT DOCUMENTS

| | | | |
|---|---|---|---|
| 5,119,833 A | | 6/1992 | Powers |
| 5,298,692 A | * | 3/1994 | Ikeda et al. ................... 181/135 |
| 5,659,620 A | * | 8/1997 | Kuhlman ....................... 381/312 |
| 6,122,388 A | * | 9/2000 | Feldman ....................... 381/322 |
| 6,339,648 B1 | | 1/2002 | McIntosh et al. |
| 6,687,377 B2 | | 2/2004 | Voix et al. |
| 6,754,357 B2 | | 6/2004 | McIntosh et al. |
| 7,688,983 B2 | | 3/2010 | Voix et al. |

FOREIGN PATENT DOCUMENTS

WO WO 03/037235 A2 5/2003

* cited by examiner

*Primary Examiner* — Patricia Bianco
*Assistant Examiner* — Camtu Nguyen
(74) *Attorney, Agent, or Firm* — Equinox IP; Franz Bonsang

(57) ABSTRACT

The in-ear device is shaped to fit a wearer's ear morphology. The device includes a main body having at least three generally convex sides, an innermost face and an outermost face. A first side is shaped to fit the tragus of a wearer's ear, and a second side is shaped to fit an antitragus of a wearer's ear. At least three tips, generally rounded, join respective two adjacent sides. The main body is within an outer ear plane substantially perpendicular to an entrance of an ear canal of a wearer's ear.

11 Claims, 3 Drawing Sheets

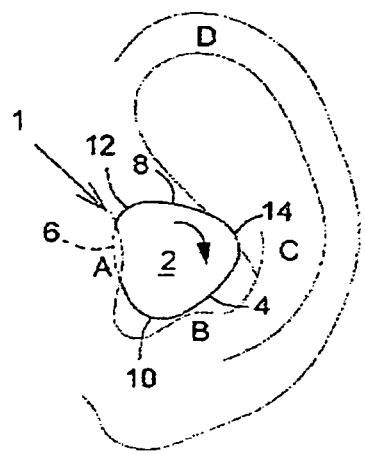
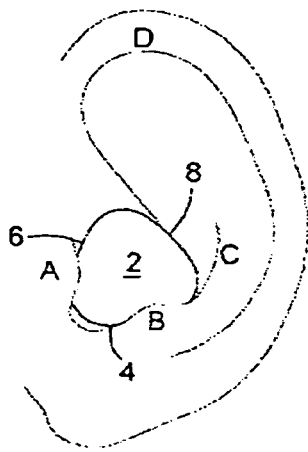
FIG.3  FIG.4
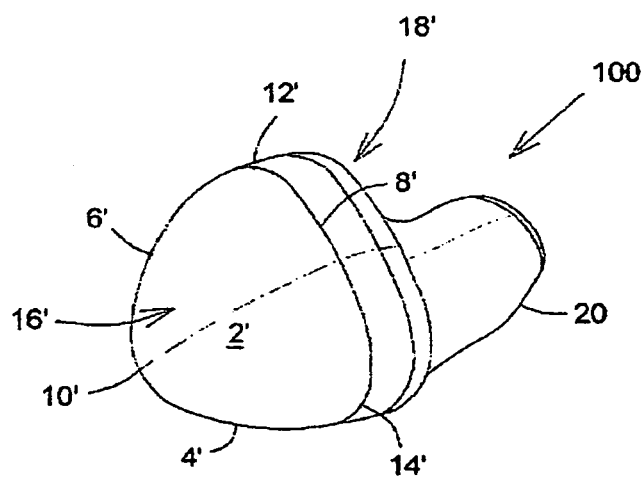
FIG.5

QUASI-TRIANGULAR IN-EAR DEVICE

CROSS REFERENCE TO RELATED APPLICATIONS

Benefit of U.S. Provisional Application for Patent Ser. No. 61/282,175 filed on Dec. 24, 2009, which is incorporated herein by reference, is hereby claimed.

FIELD OF THE INVENTION

This invention relates to in-ear devices, such as hearing protectors (earplugs), earphones, or hearing-aide devices, which have a quasi-triangular shape to provide proper fit within the human ear.

BACKGROUND OF THE INVENTION

High level sounds, and particularly the recurrence thereof, are known to cause hearing impairment, and in extreme cases, the loss of hearing. In order to avoid the hearing impairments, numerous types of hearing protectors for noise reduction have been proposed to be used in different fields and uses such as military, industrial applications and music.

One of the most common hearing protectors is foam ear plugs. Foam ear plugs are compressed and inserted into the ear canal. When the compressing pressure is interrupted, the plug expands to fit the inner morphology of the ear. Even though the placement of the plugs is simple, the decompressing forces, and the lack of proper gripping, may force them off the ear in time. Moreover, foam ear plugs must be compressed each time they will be used, forcing the user into possibly unsanitary conditions when exerting pressure in the zone that will be subsequently inserted into the ear canal.

Other common earplugs are the U-shaped headband or glasses having ear plug affixed and inwardly directed to be inserted into the ear canal of the wearer. These devices have two main drawbacks. Firstly, the presence of the headband, or the pads and temple tips in the glasses, may become disturbing to the wearer rendering the use of the ear plugs uncomfortable. Furthermore, the presence of these additional accessories does not ensure the permanence of the ear plugs in the proper position; conversely, when the headband, or the glasses, are unintentionally moved they will force the ear plugs off the ear canal, leaving the wearer exposed to undesired sound levels.

Accordingly, there is a need for an improved shaped in-ear device to enable better fit inside a wearer's ear.

BRIEF SUMMARY OF THE INVENTION

In order to overcome the limitations and problems discussed above, the main objective of the present invention is to provide a shaped in-ear device to enable better fit inside a wearer's ear.

An advantage of the present invention is to provide a shaped in-ear device that can be worn independently regardless of other protecting devices and accessories.

A further advantage of the invention is to provide an in-ear device that, once in position, will not fall off regardless of the wearer's movements.

Yet another advantage of the invention is to provide an in-ear device that can comfortably fit a wide variety of wearers.

Still another advantage of the invention is to provide an in-ear device that can comfortably fit a wearer's outer ear with a side, substantially rectilinear and slightly convex, of the main body to fit the antitragus of the ear, which is even more effective when the ear canal protrusion of the in-ear device is either pre-shaped or customized.

Yet a further advantage of the invention is to provide an in-ear device that can, when having an ear canal protrusion being either pre-shaped or customizable, be rotated 180 degrees to fit either the left or the right ear of the wearer, obviously before customization when applicable.

Another advantage of the invention is to provide an in-ear device that can, when having a body with a quasi-triangular shape, have a removable outermost surface carrying a gripping element or the like that is rotatable by 120 degrees to convert from a left in-ear preformed device into a right in-ear preformed device, and vice-versa, depending on the gripping element.

According to an aspect of the present invention, there is provided an in-ear device that comprises a main body having at least three sides, wherein a first side is shaped to fit the tragus (A) and a second side is shaped to fit the antitragus (B), the shape and dimensions of the afore-mentioned sides are such that they match the wearer's ear morphology of the tragus (A) and the antitragus (B) of a specific ear, at least three tips uniting respective two adjacent sides of the at least three sides, when both sides are properly positioned in the ear, the main body of the device is substantially on a plane perpendicular to the entrance of the ear canal (E).

Additionally, the device of the invention might include an inner protrusion on the innermost face of the main body. This inner protrusion extends inside the ear canal (E), increasing the gripping area of the device and, consequently, the stability of the device in the wearer's ear and the sound protection capability.

The stability of the device in the wearer's ear can also be increased by the optional presence of an external gripping element. When present in the device, such element might protrude from the outermost face of the main body, or from one of the remaining sides of the main body.

In one embodiment, the main body has at least one longitudinal plane of symmetry between the first side of said at least three sides being shaped to fit the tragus of a wearer's ear and the second side of said at least three sides being shaped to fit an antitragus of a wearer's ear.

Conveniently, the main body has three sides generally equal to one another, said three sides forming a device with a quasi-triangular shape of the main body. Typically, the three sides of the main body are convex.

Conveniently, the three tips of the main body are rounded. Typically, the three sides have three longitudinal planes of symmetry.

In one embodiment, the device further comprises an inner protrusion protruding outwardly from the innermost face of the main body, wherein said inner protrusion is intended to be inserted in the ear canal of the wearer. Typically, the inner protrusion substantially fits within an ear canal of the wearer.

In one embodiment, the inner protrusion of the main body has at least one longitudinal plane of symmetry, said plane symmetry coinciding with the longitudinal plane of symmetry between the first side of said at least three sides being shaped to fit the tragus of a wearer's ear and the second side of said at least three sides being shaped to fit an antitragus of a wearer's ear.

In one embodiment, the main body has an outer protrusion protruding outwardly from either the outermost face or one of the tips of the main body and defining an external gripping element. Typically, the shape of the gripping element is designed to fit the helix of a wearer's ear.

These and other advantages and objects will be apparent in view of the following detailed description in connection with the accompanying drawings.

BRIEF DESCRIPTION OF THE DRAWINGS

Further aspects and advantages of the present invention will become better understood with reference to the description in association with the following figures, in which similar references used in different figures denote similar components, wherein:

FIG. 3 is a front view of the device of FIG. 1 in the initial position inside the left-hand side ear a wearer;

FIG. 4 is a front view of the device of FIG. 1 in the final position inside the left-hand side ear a wearer;

FIG. 5 is a perspective view of another embodiment of the invention;

DETAILED DESCRIPTION OF THE PREFERRED EMBODIMENTS

Figure 1:
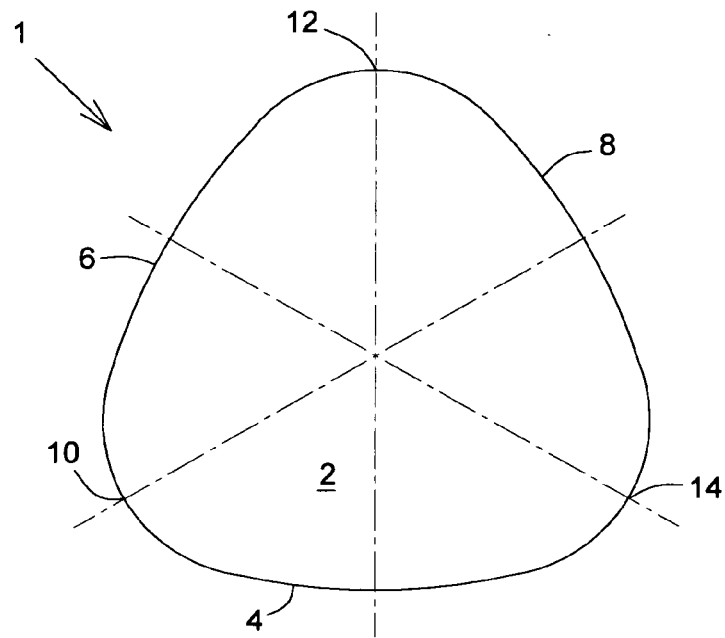
FIG. 1 is a front view of an in-ear device in accordance with an embodiment of the present invention.
Figure 2:
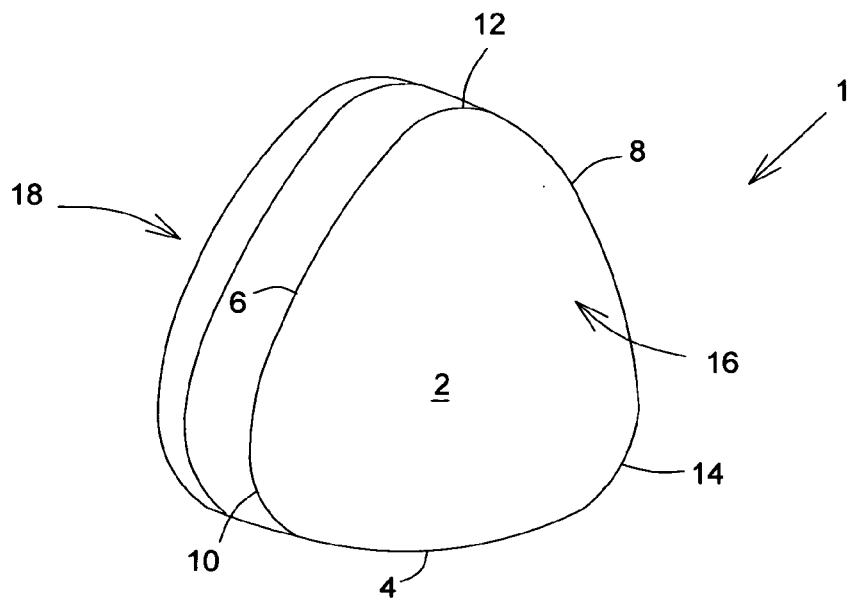
FIG. 2 is a perspective view of the embodiment of FIG. 1.

In FIGS. 1 and 2 there is depicted a specific embodiment of an in-ear device 1 of the invention comprising a main body 2 having three sides 4, 6 and 8, generally equal to one another, said three sides forming a device with a quasi-triangular shape of the main body 2. By way of example, and not a limitation, the three sides 4, 6 and 8 of the main body 2 are slightly convex (almost rectilinear); however, they might be shaped to resemble other geometrical forms. In this case, the device 1 has three longitudinal planes of symmetry represented by the dotted lines in FIG. 1. The device 1 might have at least three sides provided that at least two of the sides are designed and shaped in a way that a first side fits the tragus (A) of a wearer's ear, and the second side fits the antitragus (B) of a wearer's ear. The main body 2 also includes at least three tips. As shown in FIGS. 1 and 2, two adjacent sides are united by one of the tips 10, 12 or 14. Tips 10, 12 and 14 might have any geometrical form; preferably tips 10, 12 and 14 are rounded.

The shape and dimensions of the main body 2 are such that it can be easily positioned in the entrance of the ear canal (E), and at the same time, it will occupy the surrounding area thereof in the ear. As viewed in FIG. 2 the main body 2 includes an outermost face 16, which could be removable, and an innermost face 18.

Figure 6:
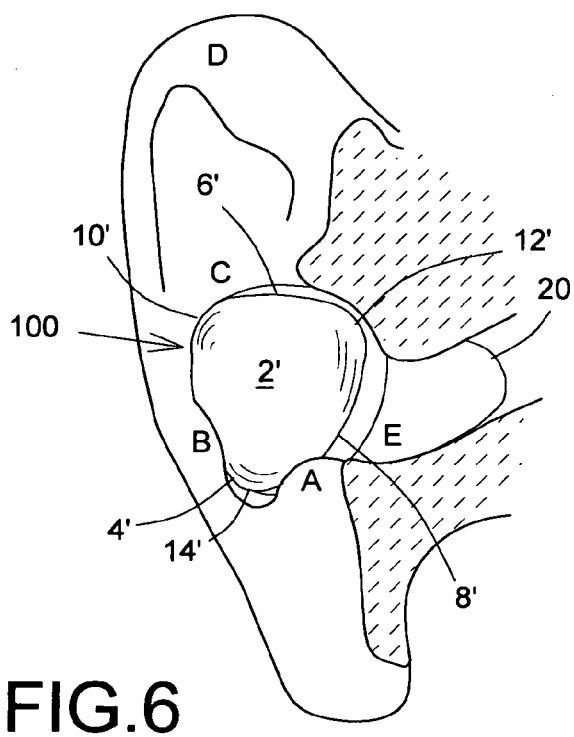
FIG. 6 is a side view of a wearer's ear including the embodiment of FIG. 5 in the final position.

In order to place the device 1 in the wearer's ear it is necessary to insert the main body 2 in the ear with the innermost face 18 facing the entrance of the ear canal (E) shown in FIG. 6. As shown in FIG. 3, the side 6 designed to fit the tragus (A) of a wearer's ear is placed in a way that both adjacent tips are near or in contact with the tragus (A) and the antitragus (B) of the left-hand side ear of a wearer. In FIG. 3 the tip 12 of the device 1 is near the tragus (A) and tip 10 is near the antitragus (B). The outermost face 16 of the main body 2 will be facing outwardly. In order to adjust the device in secure position, it is necessary to rotate it clockwise by exerting a light but firm inwardly directed pressure at the same time. When the side 6 being shaped to fit the tragus (A) of a wearer's ear and the second side 4 being shaped to fit an antitragus (B) of a wearer's ear are properly positioned in the ear, the main body 2 of the device is substantially on a plane perpendicular to the ear canal (E). In FIG. 4 it is shown the device 1 in the desired final position inside the wearer's ear. FIGS. 3 and 4 show the positioning of the device 1 inside the wearer's left ear, however, if a device 1 is designed to be placed in the wearer's right ear, the rotation will be counterclockwise. The embodiment of FIGS. 1 through 4 depicts a device 1 where the three sides 4, 6 and 8 are identical. When the sides of the invention are different, the device 1 will be designed and shaped in a way that the side 4 intended to fit the antitragus (B) always faces the lower area of the anthelix (C) of the wearer's ear in the initial position.

Referring to FIG. 5 there is an additional embodiment of the invention depicting the device 100 including an inner protrusion 20 intended to be inserted in the ear canal (E) of the wearer's ear. The inner protrusion 20 protrudes outwardly from the innermost face 18' of the main body 2' of the device 100. The inner protrusion 20 is intended to be inserted in the ear canal (E) of the wearer's ear, and it is designed and shaped to substantially fit a specific morphology of the wearer's ear.

The inner protrusion 20 of the main body 2' has at least one longitudinal plane of symmetry, said plane of symmetry coinciding with the longitudinal plane of symmetry between the side 8' of said at least three sides being shaped to fit the tragus (A) of a wearer's ear and the side 4' of said at least three sides being shaped to fit an antitragus (B) of a wearer's ear. In order to place the device 100 in the wearer's ear, the wearer just has to follow the same procedure as described above for positioning device 1; however, due to the presence of inner protrusion 20 it is also necessary to exerts a light but firm upwardly directed pressure in unison. In FIG. 6 it is shown the device 100 in the final position once it has been properly inserted.

Figure 7:
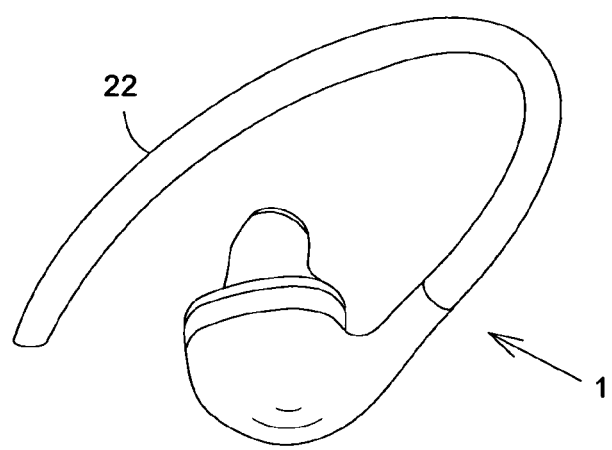
FIG. 7 is a perspective view of another embodiment of the invention.

Still another embodiment of the invention is shown in FIG. 7, wherein the device 1 further includes an optional outer protrusion defining an external gripping element 22. The gripping element 22 might protrude outwardly from on the outermost face 2 (not shown), from one of the tips from main body 2 (not shown), or as shown in FIG. 7, from one of the at least three sides 4, 6 or 8. Preferably, the gripping element 22 will protrude from the side or portion of the main body 2 which is opposite to the common tip between the side 6 of said at least three sides that fits the tragus (A) of a wearer's ear and the side 4 of said at least three sides that fits the antitragus (B) of a wearer's ear. In FIG. 7 the gripping element is represented by a curved extension, as an ear hook 22, designed to fit the rear of the helix (D) of the wearer's ear.

The above disclosed description and accompanying drawings are provided by way of example, and not a limitation. Although only few embodiments of the invention have been described in detail, those skilled in the art will appreciate that many modifications are possible in the described embodiments without departing from the spirit of this invention. For example, any of the embodiments of the present invention may be adapted for use as an earphone, or include electronic sound mufflers. In addition, it should be understood that the various features of each of the embodiments may be combined, and that the claims should not be limited to read upon the few examples shown and described herein.

Although the present invention has been described with a certain degree of particularity, it is to be understood that the disclosure has been made by way of example only and that the present invention is not limited to the features of the embodiments described and illustrated herein, but includes all variations and modifications within the scope and spirit of the invention as hereinafter claimed.

I claim:

1. An in-ear device for fitting a wearer's ear morphology, said device comprising a main body having three sides, an innermost face and an outermost face, a first side of said three sides being shaped for fitting the tragus of a wearer's ear, a second side of said three sides being shaped for fitting an antitragus of a wearer's ear, and three tips, wherein each of the three tips uniting respective two sides of said three sides, the main body being within an ear plane substantially perpendicular to an entrance of an ear canal of a wearer's ear and having at least one longitudinal plane of symmetry between the first side of said three sides being shaped for fitting the tragus of a wearer's ear and the second side of said three sides being shaped for fitting an antitragus of a wearer's ear, the three sides generally equal to one another, said three sides forming the in-ear device with a quasi-triangular shape of the main body.

2. The device of claim 1, further comprising an inner protrusion protruding outwardly from on the innermost face of the main body, wherein said inner protrusion is intended for being inserted in the ear canal of the wearer.

3. The device of claim 2, wherein the inner protrusion is substantially for fitting with an ear canal of the wearer.

4. The device of claim 3, wherein the inner protrusion of the main body has at least one longitudinal plane of symmetry, said plane of symmetry coinciding with the longitudinal plane of symmetry between the first side of said three sides being shaped for fitting the tragus of a wearer's ear and the second side of said three sides being shaped for fitting an antitragus of a wearer's ear.

5. The device of claim 1, wherein the three tips of the main body are rounded.

6. The device of claim 5, wherein the main body has three longitudinal planes of symmetry, each said longitudinal plane of symmetry being between two respective ones of said three sides adjacent to one another.

7. The device of claim 1, wherein the three sides of the main body are convex.

8. The device of claim 1, wherein the main body has an outer protrusion protruding outwardly from one of the tips of the main body and defining an external gripping element.

9. The device of claim 8, wherein the shape of the gripping element is designed for fitting the helix of a wearer's ear.

10. The device of claim 1, wherein the main body has an outer protrusion protruding outwardly from the outermost face of the main body and defining an external gripping element.

11. The device of claim 10, wherein the shape of the gripping element is designed for fitting the helix of a wearer's ear.

* * * * *